US008252777B2

(12) United States Patent
Nelson et al.

(10) Patent No.: US 8,252,777 B2
(45) Date of Patent: Aug. 28, 2012

(54) 7, 8 AND 9-SUBSTITUTED TETRACYCLINE COMPOUNDS

(75) Inventors: Mark L. Nelson, Norfolk, MA (US); Darrell J. Koza, Westerly, RI (US); Glen Rennie, Somerville, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 13/012,590

(22) Filed: Jan. 24, 2011

(65) Prior Publication Data

US 2011/0118215 A1 May 19, 2011

Related U.S. Application Data

(60) Division of application No. 12/720,258, filed on Mar. 9, 2010, now Pat. No. 7,875,649, which is a continuation of application No. 12/074,466, filed on Mar. 4, 2008, now Pat. No. 7,696,188, which is a continuation of application No. 11/454,221, filed on Jun. 16, 2006, now Pat. No. 7,361,674, which is a continuation of application No. 10/866,220, filed on Jun. 10, 2004, now Pat. No. 7,094,806, which is a continuation of application No. 10/652,713, filed on Aug. 28, 2003, now abandoned, which is a continuation of application No. 09/894,805, filed on Jun. 29, 2001, now Pat. No. 6,624,168.

(60) Provisional application No. 60/216,656, filed on Jul. 7, 2000.

(51) Int. Cl.
*C07C 237/26* (2006.01)
*A61K 31/66* (2006.01)

(52) U.S. Cl. ........................................ 514/152; 552/203

(58) Field of Classification Search .................. 552/203; 514/152
See application file for complete search history.

(56) References Cited

U.S. PATENT DOCUMENTS

| | | | |
|---|---|---|---|
| 2,980,584 A | 4/1961 | Hammer | |
| 2,990,331 A | 6/1961 | Neumann et al. | |
| 3,007,965 A | 11/1961 | Growich, Jr. et al. | |
| 3,062,717 A | 11/1962 | Hammer | |
| 3,165,531 A | 1/1965 | Blackwood et al. | |
| 3,226,436 A | 12/1965 | Petisi et al. | |
| RE26,253 E | 8/1967 | Petisi et al. | |
| 3,338,963 A | 8/1967 | Petisi et al. | |
| RE26,271 E | 9/1967 | Boothe et al. | |
| 3,341,585 A | 9/1967 | Bitha et al. | |
| 3,345,379 A | 10/1967 | Martell et al. | |
| 3,345,410 A | 10/1967 | Winterbottom et al. | |
| 3,360,561 A | 12/1967 | Zambrano | |
| 3,373,193 A | 3/1968 | Schroeder et al. | |
| 3,388,162 A | 6/1968 | Winterbottom et al. | |
| 3,397,230 A | 8/1968 | Winterbottom et al. | |
| 3,403,179 A | 9/1968 | Zambrano | |
| 3,454,697 A | 7/1969 | Joyner et al. |
| 3,483,251 A | 12/1969 | Zambrano |
| 3,518,306 A | 6/1970 | Martell et al. |
| 3,557,280 A | 1/1971 | Weber et al. |
| 3,579,579 A | 5/1971 | Ross et al. |
| 3,609,188 A | 9/1971 | Esse et al. |
| 3,674,859 A | 7/1972 | Beutel et al. |
| 3,849,493 A | 11/1974 | Conover et al. |
| 3,862,225 A | 1/1975 | Conover et al. |
| 3,901,942 A | 8/1975 | Bernardi et al. |
| 3,957,980 A | 5/1976 | Noseworthy |
| 4,018,889 A | 4/1977 | Armstrong |
| 4,024,272 A | 5/1977 | Rogalski et al. |
| 4,126,680 A | 11/1978 | Armstrong |
| 5,064,821 A | 11/1991 | Levy |
| 5,248,797 A | 9/1993 | Sum |
| 5,281,628 A | 1/1994 | Hlavka et al. |
| 5,284,963 A | 2/1994 | Sum et al. |
| 5,326,759 A | 7/1994 | Hlavka et al. |
| 5,328,902 A | 7/1994 | Sum et al. |
| 5,371,076 A | 12/1994 | Lee et al. |
| 5,380,888 A | 1/1995 | Sum et al. |
| 5,386,041 A | 1/1995 | Sum et al. |
| 5,401,729 A | 3/1995 | Sum et al. |
| 5,401,863 A | 3/1995 | Hlavka et al. |
| 5,420,272 A | 5/1995 | Sum et al. |
| 5,430,162 A | 7/1995 | Sum et al. |
| 5,442,059 A | 8/1995 | Sum et al. |
| 5,457,096 A | 10/1995 | Sum et al. |
| 5,466,684 A | 11/1995 | Sum et al. |
| 5,494,903 A | 2/1996 | Hlavka et al. |
| 5,495,018 A | 2/1996 | Sum et al. |

(Continued)

FOREIGN PATENT DOCUMENTS

EP 0535346 A1 4/1993

(Continued)

OTHER PUBLICATIONS

Beereboom et al. Journal of the American Chemical Society (1960), 82, 1003-4.*
Resnick et al. Current Therap. Res. Clin. Exptl. (1965), 7(8), 443-50.*
Koza et al. Organic Letters, (2000), 2(6), 815-817.*
Alves, A.B., et al., "Short synthesis of azafluorenone alkaloids using transition metal-catalyzed cross coupling tactics," *Tetrahedron Lett.*, vol. 29(18):2135-36 (1988).
Berge, S.M., et al., "Pharmaceutical Salts," *J. Pharm.Sci.*, vol. 66(1):1-19 (1977).
Boothe, J., et al., "6-Deoxytetracyclines. I. Chemical Modification by Electrophilic Substitution," *J. Am. Chem. Soc.*, vol. 82:1253-4 (1960).
Cheng, W., et al., "Synthetic connections to the aromatic directed metalation reaction. Iterative ortho metalation-cross coupling tactics for the construction of polyphenyls," *Tetrahedron Lett.*, vol. 28(43):5097-98 (1987).

(Continued)

*Primary Examiner* — Kahsay T. Habte
(74) *Attorney, Agent, or Firm* — Mintz Levin Cohn Ferris Glovsky and Popeo, P.C.; Heidi A. Erlacher; Yongjun Zhang

(57) ABSTRACT

7, 8 and 9-substituted tetracycline compounds, methods of treating tetracycline responsive states, and pharmaceutical compositions containing the 7, 8 and 9-substituted tetracycline compounds are described.

14 Claims, No Drawings

U.S. PATENT DOCUMENTS

| | | | |
|---|---|---|---|
| 5,495,030 A | 2/1996 | Sum et al. |
| 5,495,031 A | 2/1996 | Sum et al. |
| 5,512,553 A | 4/1996 | Sum et al. |
| 5,529,990 A | 6/1996 | Hlavka et al. |
| 5,530,117 A | 6/1996 | Hlavka et al. |
| 5,532,227 A | 7/1996 | Golub et al. |
| 5,567,692 A | 10/1996 | Sum et al. |
| 5,567,693 A | 10/1996 | Backer et al. |
| 5,639,742 A | 6/1997 | Lee et al. |
| 5,675,030 A | 10/1997 | Krishnan et al. |
| 5,789,395 A | 8/1998 | Amin et al. |
| 5,834,450 A | 11/1998 | Su |
| 5,886,175 A | 3/1999 | Sum et al. |
| 6,500,812 B2 | 12/2002 | Nelson et al. |
| 6,506,740 B1 | 1/2003 | Ashley et al. |
| 6,617,318 B1 | 9/2003 | Nelson et al. |
| 6,624,168 B2 | 9/2003 | Nelson et al. |
| 6,642,270 B2 | 11/2003 | Nelson et al. |
| 6,683,068 B2 | 1/2004 | Nelson et al. |
| 6,818,634 B2 | 11/2004 | Nelson et al. |
| 6,818,635 B2 | 11/2004 | Nelson et al. |
| 6,833,365 B2 | 12/2004 | Levy et al. |
| 6,841,546 B2 | 1/2005 | Draper et al. |
| 6,846,939 B2 | 1/2005 | Nelson et al. |
| 6,849,615 B2 | 2/2005 | Nelson et al. |
| 7,001,918 B2 | 2/2006 | Huss et al. |
| 7,045,507 B2 | 5/2006 | Draper et al. |
| 7,056,902 B2 | 6/2006 | Nelson et al. |
| 7,067,681 B2 | 6/2006 | Nelson et al. |
| 7,094,806 B2 | 8/2006 | Nelson et al. |
| 7,208,482 B2 | 4/2007 | Garcia-Luzon et al. |
| 7,521,437 B2 | 4/2009 | Nelson et al. |
| 2002/0128237 A1 | 9/2002 | Nelson et al. |
| 2002/0160987 A1 | 10/2002 | Ashley et al. |
| 2003/0195174 A1 | 10/2003 | Ashley et al. |
| 2004/0002481 A1 | 1/2004 | Ashley et al. |
| 2004/0024548 A1 | 2/2004 | Genther et al. |
| 2004/0033966 A1 | 2/2004 | Redkar et al. |
| 2004/0063674 A1 | 4/2004 | Levy et al. |
| 2004/0067912 A1 | 4/2004 | Hlavka et al. |
| 2004/0092490 A1 | 5/2004 | Draper et al. |
| 2004/0138183 A1 | 7/2004 | Nelson et al. |
| 2004/0176334 A1 | 9/2004 | Nelson et al. |
| 2004/0214800 A1 | 10/2004 | Levy et al. |
| 2004/0214801 A1 | 10/2004 | Nelson et al. |
| 2004/0242548 A1 | 12/2004 | Draper et al. |
| 2004/0266740 A1 | 12/2004 | Huss et al. |
| 2005/0020545 A1 | 1/2005 | Draper et al. |
| 2005/0026875 A1 | 2/2005 | Nelson et al. |
| 2005/0026876 A1 | 2/2005 | Nelson et al. |
| 2005/0038002 A1 | 2/2005 | Nelson et al. |
| 2005/0070510 A1 | 3/2005 | Draper et al. |
| 2005/0119235 A1 | 6/2005 | Nelson et al. |
| 2005/0137174 A1 | 6/2005 | Ohemeng et al. |
| 2005/0143352 A1 | 6/2005 | Nelson et al. |
| 2005/0143353 A1 | 6/2005 | Nelson et al. |
| 2005/0215532 A1 | 9/2005 | Levy et al. |
| 2005/0245491 A9 | 11/2005 | Hlavka et al. |
| 2005/0250744 A1 | 11/2005 | Levy et al. |
| 2005/0267079 A1 | 12/2005 | Hlavka et al. |
| 2005/0282787 A1 | 12/2005 | Myers et al. |
| 2005/0288262 A1 | 12/2005 | Bandarage et al. |
| 2006/0003971 A1 | 1/2006 | Nelson |
| 2006/0084634 A1 | 4/2006 | Huss et al. |
| 2006/0089336 A1 | 4/2006 | Nelson et al. |
| 2006/0148765 A1 | 7/2006 | Nelson et al. |
| 2006/0166944 A1 | 7/2006 | Berniac et al. |
| 2006/0166945 A1 | 7/2006 | Abato et al. |
| 2006/0166946 A1 | 7/2006 | Nelson et al. |
| 2006/0194773 A1 | 8/2006 | Levy et al. |
| 2006/0205698 A1 | 9/2006 | Nelson et al. |
| 2006/0281717 A1 | 12/2006 | Berniac et al. |
| 2007/0093455 A1 | 4/2007 | Abato et al. |
| 2008/0070873 A1 | 3/2008 | Alekshun et al. |
| 2008/0118979 A1 | 5/2008 | Draper et al. |
| 2008/0287401 A1 | 11/2008 | Johnston et al. |
| 2008/0312193 A1 | 12/2008 | Assefa et al. |
| 2009/0118269 A1 | 5/2009 | Berniac et al. |
| 2009/0156842 A1 | 6/2009 | Seyedi et al. |

FOREIGN PATENT DOCUMENTS

| | | |
|---|---|---|
| EP | 0536515 | 4/1993 |
| EP | 0582788 A1 | 2/1994 |
| EP | 0582790 A1 | 2/1994 |
| EP | 0582810 A1 | 2/1994 |
| EP | 0582829 A1 | 2/1994 |
| EP | 0618190 A1 | 10/1994 |
| GB | 951252 A | 3/1964 |
| GB | 1469384 A | 4/1977 |
| WO | WO-9634852 A1 | 11/1996 |
| WO | WO-9937306 A1 | 7/1999 |
| WO | WO-0028983 A1 | 5/2000 |
| WO | WO-2005082860 A1 | 9/2005 |

OTHER PUBLICATIONS

Koza et al., "Palladium Catalyzed C-N Bond Formation in the Synthesis of 7-Amino-Substituted Tetracyclines", *JOC Note*, vol. 67:5025-5027 (2002).

Koza et al., "Synthesis and Biological Evaluation of 9-Substituted Tetracycline Derivatives", *Bio. and Med. Chem. Ltrs.*, vol. 12:2163-2165 (2002).

Koza, D.J., "Synthesis of 7-substituted tetracycline derivatives," *Organic Lett.*, vol. 2:815-17 (2000).

Koza, D.J., "The synthesis of 8-substituted tetracycline derivatives, the first 8-position carbon-carbon bond," *Tetrahedron Lett.*, vol. 41:5017-20 (2000).

Martell, et al., "The 6-deoxytetracyclines. VII. Alkylated aminotetracyclines possessing unique antibacterial activity," *J. Med. Chem.*, vol. 10(3):359-63 (1967).

Muller, D., et al., "A new strategy for the synthesis of biflavonoids via arylboronic acids," *Tetrahedron Lett.*, vol. 32(20):2229-32 (1991).

Murahashi, S-I, et al., "Stereoselective synthesis of alkenes and alkenyl sulfides from alkenyl halides using palladium and ruthenium catalyst," *J. Org. Chem.*, vol. 44(14):2408 (1979).

Sharp, M.J., et al., "Synthetic connections to the aromatic directed metalation reaction. Functionalized aryl boronic acids by ipso borodesilylation. General syntheses of unsymmetrical biphenyls and m-terphenyls," *Tetrahedron Lett.*, vol. 28(43):5093-96 (1987).

Silverman, "The Organic Chemistry of Drug Design and Drug Action," *Adademic Press*, Chp. 8, pp. 352-400 (1992).

Sum et al., "Synthesis of Novel Tetracycline Derivatives with Substitution at the C-8 Position", *Tetrahedron Lett.*, vol. 35(12):1835-1836 (1994).

Sum, P., "Glycylclines. I. A new generation of potent antibacterial agents through modification of 9-aminotetracyclines," *J. Med. Chem.* vol. 37(1):184-8 (1994).

Sum, P.E., et al., "Synthesis and structure activity relationship of novel glycylcycline derivatives leading to the discovery of GAR 936," *Bioorg. Med. Chem. Lett.*, vol. 9(10): 1459-62 (1999).

Tamao, K., et al., "Nickel phosphine complex-catalyzed Grignard coupling. I. Cross-coupling of alkyl, aryl, and alkenyl Grignard reagents with aryl and alkenyl halides: general scope and limitations," *Bull. Chem. Soc. Jpn.*, vol. 49(7):1958-69 (1976).

Van den Bogart, et al., "Doxycycline in combination chemotherapy of a rat leukemia," *Cancer Res.*, vol. 48:6686-6690 (1988).

Barden, Timothy C. et al., "Glycylcyclines". 3. 9-Aminodoxycyclinescarboxamides, *J. Med Chem.* 1994, 37, 3205-3211.

\* cited by examiner

7, 8 AND 9-SUBSTITUTED TETRACYCLINE COMPOUNDS

RELATED APPLICATIONS

This application is a divisional of U.S. application Ser. No. 12/720,258, filed Mar. 9, 2010; which is a continuation of U.S. application Ser. No. 12/074,466, filed Mar. 4, 2008; which is a continuation of U.S. application Ser. No. 11/454,221, filed Jun. 16, 2006; which is a continuation of U.S. application Ser. No. 10/866,220, filed Jun. 10, 2004; which is a continuation of U.S. application Ser. No. 10/652,713, filed Aug. 28, 2003; which is a continuation of U.S. application Ser. No. 09/894,805, filed Jun. 29, 2001; which claims the benefit of U.S. Provisional Patent Application No. 60/216,656, filed Jul. 7, 2000. This application is related to International Patent Application Serial No.: PCT/US00/21366, filed Aug. 4, 2000. The entire contents of all the aforementioned patent applications are hereby incorporated herein by reference.

BACKGROUND OF THE INVENTION

The development of the tetracycline antibiotics was the direct result of a systematic screening of soil specimens collected from many parts of the world for evidence of microorganisms capable of producing bactericidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, including conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines and tetracycline analogue compositions as antibiotics of choice.

SUMMARY OF THE INVENTION

The invention pertains, at least in part, to 7-, 8- or 9-substituted tetracycline compounds of the formula:

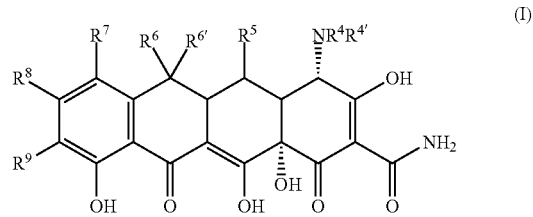

wherein:
$R^4$ and $R^{4'}$ are each methyl;
$R^5$ is hydrogen or hydroxyl;
$R^6$ and $R^{6'}$ are each independently hydrogen, methyl, or hydroxyl;
$R^7$ is hydrogen, lower alkenyl, lower alkynyl, phenyl, halophenyl, acyl, heteroaryl, phenylalkynyl, or dimethylamino; and
$R^8$ is hydrogen, phenyl, nitrophenyl, halo, or lower alkynyl; and
$R^9$ is hydrogen, amino, acetamide, or lower alkynyl; and
provided that at least one of $R^7$, $R^8$, or $R^9$ is not hydrogen; and pharmaceutically acceptable salts thereof.

In an embodiment, the tetracycline compound of the invention is a tetracycline derivative wherein $R^5$ is hydrogen, $R^6$ is methyl, $R^{6'}$ is hydroxyl, and $R^7$ is phenyl.

In another embodiment, the tetracycline compound of the invention is a doxycycline derivative, wherein $R^5$ is hydroxyl, $R^6$ is methyl, and $R^{6'}$ is hydrogen. In a further embodiment, the doxycycline derivative comprises $R^7$ groups such as lower alkenyl (e.g., ethenyl), lower alkynyl (e.g., ethynyl), heteroaryl (e.g., furanyl, dioxenyl, pyrazinyl, or pyridinyl), phenyl, halophenyl or phenylalkynyl. Doxycycline derivatives also may comprise $R^8$ groups such as hydrogen, halogen (e.g., bromine), lower alkynyl (e.g., ethynyl), phenyl, or nitrophenyl. In certain embodiments, $R^7$ is ethenyl or ethynyl; and $R^8$ and $R^9$ are each hydrogen. In another, $R^7$ is phenyl, halophenyl or phenylalkynyl; and $R^8$ and $R^9$ are each hydrogen. Alternatively, $R^7$ is hydrogen, $R^8$ is halo, phenyl, or nitrophenyl, and $R^9$ is hydrogen. Further, $R^7$ may be hydrogen, $R^8$ phenyl, and $R^9$ amino.

In another embodiment, the tetracycline compound of the invention is a demeclocycline derivative, wherein $R^5$ is hydrogen, $R^6$ is hydroxyl, $R^{6'}$ is hydrogen, and $R^7$ is phenyl. In another embodiment, the tetracycline compound of the invention is a minocycline derivative wherein $R^5$ is hydroxyl, $R^6$ is hydrogen, $R^{6'}$ is hydrogen, $R^7$ is dimethylamino, and $R^9$ is lower alkynyl (e.g., ethynyl).

The invention also pertains to a method for treating a tetracycline responsive state in a mammal, by administering to a mammal a compound of formula I. In another aspect, the invention relates to the use of a compound of formula I to treat a tetracycline responsive state. The invention also pertains to pharmaceutical compositions comprising a compound of formula I, and to the use of a compound of formula I in the manufacture of a medicament to treat a tetracycline responsive state.

DETAILED DESCRIPTION OF THE INVENTION

The invention pertains to, at least in part, to 7-, 8- or 9-substituted tetracycline compounds of the formula:

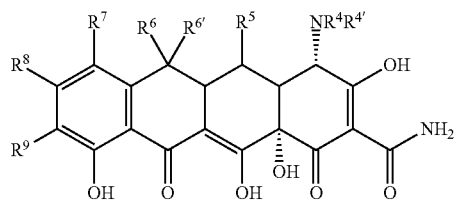

wherein:

$R^4$ and $R^{4'}$ are each methyl;

$R^5$ is hydrogen or hydroxyl;

$R^6$ and $R^{6'}$ are each independently hydrogen, methyl, or hydroxyl;

$R^7$ is hydrogen, lower alkenyl, lower alkynyl, phenyl, halophenyl, acyl, phenylalkynyl, heteroaryl, or dimethylamino; and $R^8$ is hydrogen, phenyl, nitrophenyl, halo, or lower alkynyl;

and $R^9$ is hydrogen, amino, acetamide, or lower alkynyl; and provided that at least one of $R^7$, $R^8$, or $R^9$ is not hydrogen; and pharmaceutically acceptable salts thereof.

The term "tetracycline compound" includes compounds with a similar ring structure to tetracycline, such as those included in formula I. Some examples of tetracycline compounds which can be modified include a substituent at position 7, 8 or 9 include tetracycline, demeclocycline, sancycline, and doxycycline; however, other derivatives and analogues comprising a similar ring structure are also included. Table 1 depicts the structure of tetracycline, demeclocycline, sancycline, and doxycycline.

TABLE I

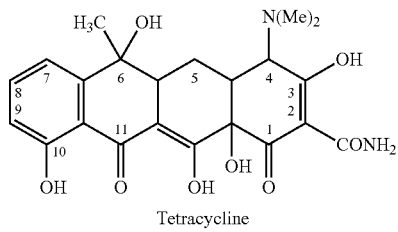

Tetracycline

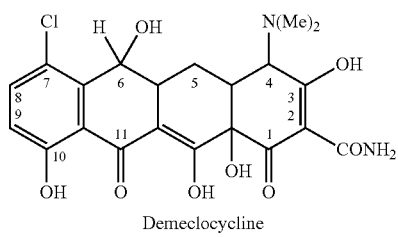

Demeclocycline

TABLE I-continued

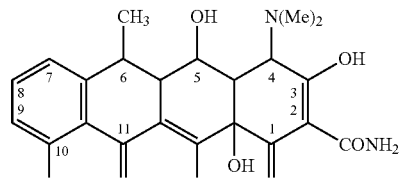

Doxycycline

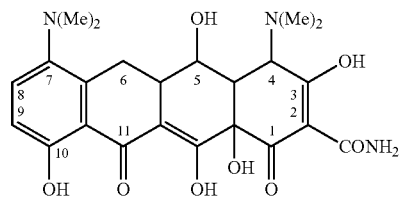

Minocycline

The term "7, 8 or 9-substituted tetracycline compounds" includes tetracycline compounds with at least one substituent at the 7, 8 and/or 9 position, as described in formula I. In an embodiment, the substituted tetracycline compound is substituted tetracycline derivative (e.g., wherein $R^4$ and $R^{4'}$ are methyl, $R^5$ is hydrogen, $R^6$ is methyl and $R^{6'}$ is hydroxyl); substituted doxycycline derivative (e.g., wherein $R^4$ and $R^{4'}$ are methyl, $R^5$ is hydroxyl $R^6$ is methyl and $R^{6'}$ is hydrogen); substituted demeclocycline derivative (e.g., $R^5$ is hydrogen, $R^6$ is hydroxyl, $R^{6'}$ is hydrogen, $R^7$ is chloro and $R^4$ and $R^{4'}$ are each methyl); or substituted minocycline derivative (wherein $R^4$ and $R^{4'}$ are methyl; $R^5$ is hydrogen and $R^6$ and $R^{6'}$ are hydrogen atoms).

In an embodiment, the substituted tetracycline compound of the invention is a tetracycline derivative, wherein $R^5$ is hydrogen, $R^6$ is methyl, $R^{6'}$ is hydroxyl, and $R^7$ is phenyl. Examples of such tetracycline compounds include 7-phenyl tetracycline.

In another embodiment, the substituted tetracycline compound of the invention is a doxycycline derivative, wherein $R^5$ is hydroxyl, $R^6$ is methyl, and $R^{6'}$ is hydrogen.

In an alternate embodiment, doxycycline derivatives of tetracycline compounds of the invention include compounds wherein $R^7$ is hydrogen, $R^8$ is halo, phenyl, or nitrophenyl, and $R^9$ is hydrogen. In another alternate embodiment, $R^7$ is hydrogen, $R^8$ is phenyl or lower alkynyl (e.g., ethynyl), and $R^9$ is amino. In yet another alternate embodiment, $R^7$ and $R^8$ are both hydrogen and $R^9$ is acetamide.

In further embodiments of the invention, the doxycycline derivatives include compounds wherein $R^7$ is lower alkenyl (e.g., ethenyl), lower alkynyl (e.g., ethynyl), phenyl, heteroaryl (e.g., furanyl, pyrazinyl, pyridinyl, or dioxenyl), acyl (e.g., lower alkyl carbonyl, e.g., methylcarbonyl), halophenyl or phenylalkynyl (e.g., phenylethynyl); and $R^8$ and $R^9$ are each hydrogen.

Examples of such tetracycline compound which are doxycycline derivatives include 7-ethenyl doxycycline, 7-ethynyl doxycycline, 7-phenyl doxycycline, 7-(4-fluorophenyl) doxycycline, 7-phenylethynyl doxycycline, 9-acetamide doxycycline, 8-phenyl doxycycline, 8-bromo doxycycline, 8-(p-nitrophenyl) doxycycline, 8-ethynyl-9-amino doxycycline, 8-phenyl-9-amino doxycycline, 7-(1,4-dioxenyl) doxycycline, 7-(2-furanyl) doxycycline, 7-(2-pyrazinyl) doxycycline, 7-(2-pyridinyl) doxycycline, and 7-acyl doxycycline.

In another embodiment, the tetracycline compound of the invention is a demeclocycline derivative, wherein $R^5$ is hydrogen, $R^6$ is hydroxyl, $R^{6'}$ is hydrogen, $R^7$ is phenyl, and $R^8$ and $R^9$ are both hydrogen. Examples of demeclocycline derivatives include 7-phenyl demeclocycline.

In another embodiment, the tetracycline compound of the invention is a minocycline derivative, wherein $R^5$ is hydroxyl, $R^6$ is hydrogen, $R^{6'}$ is hydrogen, $R^7$ is dimethylamino, $R^8$ is hydrogen, and $R^9$ is lower alkynyl (e.g., ethynyl). Examples include 9-ethynyl minocycline.

Compounds of the invention can be synthesized by transition metal catalyzed coupling of tetracyclines halogenated at the 7-, 8-, or 9-position. For example, many reactions between aryl halides and various reactive species have been developed using transition metal catalysis. Coupling of aryl halides or triflates with main group organometallics with oxidate addition—transmetallation—reductive elimination reactions has been developed and occurs using a wide range of catalysts, such as $Pd(Pd_3)_4$, $Pd(dba)_2$, $PdCl_2$, $Pd(OAc)_2$, and $PdCl_2(CH_3CN)_2$. Ligands such as $PPh_3$ or $AsPh_3$ may be added to form catalysts in situ with palladium species such as $Pd(dba)_2$ or $PdCl_2$. Furthermore, copper salts, such as CuCN or CuI may also be added to further enhance the reaction. An example of a coupling using a halogenated tetracycline compound is shown in Scheme 1. In Scheme 1, X is bromine or iodine.

SCHEME 1

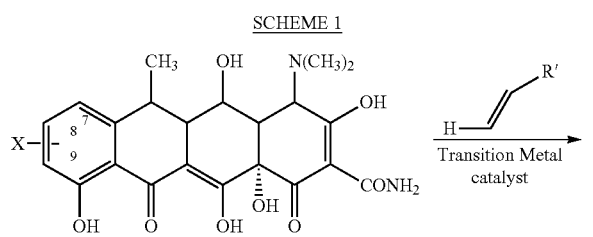

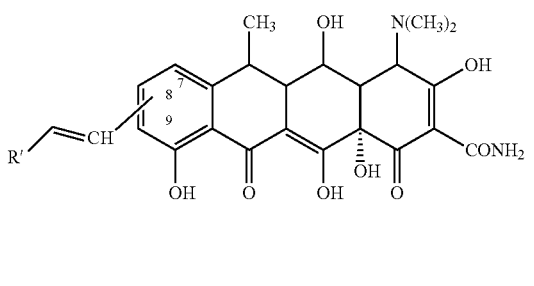

The substituted tetracycline compounds of the invention can be synthesized using organotin reagents, halogenated or triflate tetracycline compounds, and an appropriate catalyst (e.g., palladium). Examples of tin reagents include, for example, ethenyl tributyltin, ethynyl tributyltin, phenyl tributyltin, ethenyl trimethyl tin, ethynyl trimethyl tin, etc. These Stille type couplings are run by adding the transition metal (e.g., palladium) catalyst to a solution of the halogenated or triflate tetracycline compound and the organotin reagent in polar solvents. Stille type couplings with alkynyl and alkenyl tin reagents are shown in Scheme 2, wherein X is a halogen or a triflate group.

SCHEME 2

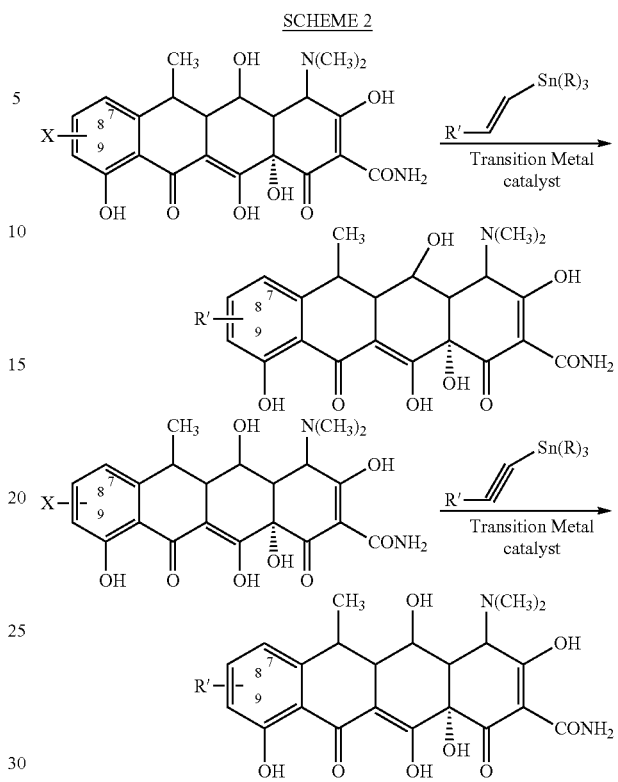

Other methods of synthesizing the 7-, 8-, and 9-substituted tetracycline compounds of the invention include coupling halogenated tetracycline compounds to boronic acids using Suzuki type couplings (M. J. Sharp et al. *Tetrahedron Lett.* 28 (1987) 5093; W. Cheng, et al. *Tetrahedron Lett.* 28 (1987) 5097; Alves, A. B. et al. *Tetrahedron Lett.* 29 (1988) 2135; D. Muller, et al. *Tetrahedron Lett.* 32 (1991) 2135), Grignard reagents (K. Tamao et al. *Bull. Chem. Soc. Jpn.* 49 (1976) 1958), or organolithium reagents (S.-I. Murahashi et al., *J. Org. Chem.* 44 (1979) 2408) and a transition metal catalyst, as shown in Scheme 3.

SCHEME 3

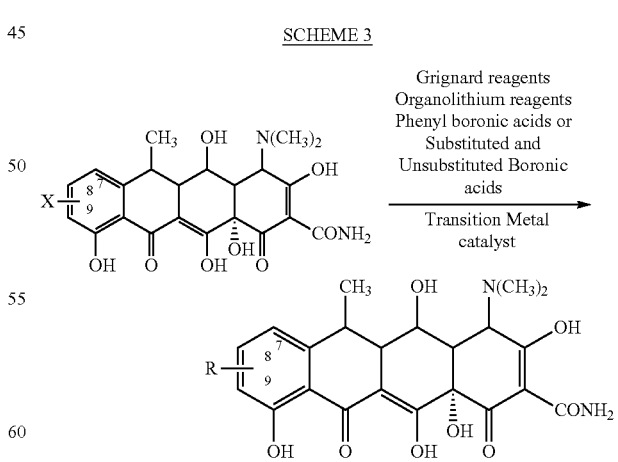

8-halogenated tetracycline compounds can be synthesized via azidotetracyclines. The protonolysis of the aryl azides produces 8-halo-9-amino tetracycline in good yield.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which comprise oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids.

The term "aryl" includes groups with aromaticity, including 5- and 6-membered single-ring aromatic groups that may include from zero to four heteroatoms as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl). In a further embodiment, the term "heteroaryl" refers to pyrazinyl, pyridinyl, furanyl, and dioxenyl groups.

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. In a further embodiment, the term "lower alkenyl" refers to moieties with 2-5 carbons. Advantageous lower alkenyl groups include ethenyl groups.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure, e.g., methyl, ethyl, propyl, butyl and pentyl. "Lower alkenyl" and "lower alkynyl" have chain lengths of, for example, 2-5 carbon atoms, e.g., ethenyl, ethynyl, propenyl, propynyl, butenyl, butynyl, pentenyl, and pentynyl.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, acylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "amine" or "amino" includes compounds where a nitrogen atom is covalently bonded to at least one carbon or heteroatom. The term "alkylamino" includes groups and compounds wherein the nitrogen is bound to at least one additional alkyl group. The term "dialkylamino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "dioxenyl" refers to moieties of the formula:

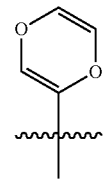

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "halo" includes, for example, substituents such as chlorine, fluorine, bromine, or iodine, as well as mono-, di- or tri-halgentated lower alkyl group, e.g., mono-, di- or tri-halogenated methyl groups. In certain embodiments, the halo substitution of the phenyl substituent enhances the ability of the tetracycline compound to perform its intended function, e.g., treat tetracycline responsive states.

The term "heteroatom" includes atoms of any element other than carbon or hydrogen. Examples of heteroatoms include nitrogen, oxygen, sulfur and phosphorus.

The term "hydroxy" or "hydroxyl" includes groups with an —OH or —O⁻.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "thiocarbonyl" or "thiocarboxy" includes compounds and moieties which contain a carbon connected with a double bond to a sulfur atom.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a hydroxyl group, can be esterified, e.g., with a carboxylic acid group to yield an ester. When the ester is administered to a subject, the ester is cleaved, enzymatically or non-enzymatically, reductively or hydrolytically, to reveal the hydroxyl group.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

The invention also features a method for treating a tetracycline compound responsive state in a subject, by administering to the subject a 7-, 8-, or 9-substituted tetracycline compound of the invention, e.g., a compound of formula I. Preferably, an effective amount of the tetracycline compound is administered. Examples of 7, 8 or 9-substituted tetracycline compounds of the invention include 7-phenyl tetracycline, 7-ethenyl doxycycline 7-ethynyl doxycycline, 7-phenyl doxycycline, 7-(4-fluorophenyl) doxycycline, 7-phenylethynyl doxycycline, 9-acetamide doxycycline, 8-phenyl doxycycline, 8-bromo doxycycline, 8-(p-nitrophenyl) doxycycline, 8-ethynyl-9-amino doxycycline, 8-phenyl-9-amino doxycycline, 7-phenyl demeclocycline, and 9-ethynyl minocycline, 7-(1,4-dioxenyl) doxycycline, 7-(2-furanyl) doxycycline, 7-(2-pyrazinyl) doxycycline, 7-(2-pyridinyl) doxycycline, and 7-acetyl doxycycline.

The language "tetracycline compound responsive state" includes states which can be treated, prevented, or otherwise ameliorated by the administration of a tetracycline compound of the invention. Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227, incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)).

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document M7-A2*, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

In one embodiment, the pharmaceutical composition comprises a 7-, 8 or 9-substituted tetracycline compound of the invention, e.g., of formula I. In a further embodiment, the 7, 8 or 9-substituted tetracycline compound is 7-phenyl tetracycline, 7-ethenyl doxycycline 7-ethynyl doxycycline, 7-phenyl doxycycline, 7-(4-fluorophenyl) doxycycline, 7-phenylethynyl doxycycline, 9-acetamide doxycycline, 8-phenyl doxycycline, 8-bromo doxycycline, 8-(p-nitrophenyl) doxycycline, 8-ethynyl-9-amino doxycycline, 8-phenyl-9-amino doxycycline, 7-phenyl demeclocycline, and 9-ethynyl minocycline, 7-(1,4-dioxenyl) doxycycline, 7-(2-furanyl) doxycycline, 7-(2-pyrazinyl) doxycycline, 7-(2-pyridinyl) doxycycline, or 7-acetyl doxycycline.

The language "pharmaceutically acceptable carrier" includes substances capable of being coadministered with the tetracycline compound(s), and which allow both to perform their intended function, e.g., treat or prevent a tetracycline compound responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, for the preparation of a medicament. The medicament may include a pharmaceutically acceptable carrier and the tetracycline compound is an effective amount, e.g., an effective amount to treat a tetracycline responsive state.

In yet another embodiment, the invention also pertains to the use of a tetracycline compound of formula I to treat a tetracycline responsive state, e.g., in a subject, e.g., a mammal, e.g., a human.

Compounds of the invention may be made as described below, with modifications to the procedure below within the skill of those of ordinary skill in the art.

Example 1

Synthesis of 7-, 8- and 9-Substituted Tetracycline Compounds 7- and 9-Iodo Tetracycline Compounds Five grams of a tetracycline compound was dissolved in 85 mL of concentrated sulfuric acid that was cooled to 0° C. (on ice). N-iodosuccinimide (NIS) was added to the reaction in 300 mg portions every 15 minutes. The reaction proceeded for 5 hours before being removed from the ice bath. The reaction mixture was then analyzed by HPLC and TLC, showed the product of D-ring iodotetracyclines. After the reaction was complete, the sulfuric acid was dripped slowly 1 L of ice water and extracted 7 times with 300 mL of n-butanol. The solvent was removed in vacuo to produce a mixture of three products. The 7-iodo regioisomer, 9-regioisomer and 7,9-diiodo tetracycline compound derivatives were purified by preparative HPLC chromatography and by methods known in the art.

9-$NO_2$ Doxycycline 1.0 g of doxycycline HCl was dissolved in concentrated $H_2SO_4$ (5 ml) and $NaNO_3$ (1.1 eq) was added over 1 minute. The reaction was stirred for 1 hour and subsequently dripped into cold, rapidly stirred ether (500 ml). The precipitate was washed with ether and dried in vacuum to yield 9-$NO_2$ doxycycline without further purification.

9-$NH_2$ Doxycycline:

9-$NO_2$ doxycycline (1 g) was dissolved in methanol (50 ml) and poured into a Parr apparatus with 100 mg of 10% Pd/C. The reaction was charged with $H_2$ and shaken for 2 hours. The 9-amino doxycycline was separated by preparative apic purification to produce 9-$NH_2$ doxycycline and 7-$NH_2$ doxycycline in a 7:2 ratio.

9-$N_2$ Doxycycline

9-$NH_2$ doxycycline (1.5 g) was dissolved in 50 ml of 0.1N methanol HCl and 2.2 ml of butyl nitrate was subsequently added. The reaction was stirred for 1 hour, then the product was precipitated in 400 mL of dry ether to produce the 9-diazonium salt of doxycycline 9-Azido Doxycycline Sodium azide (0.126 g) was added to a warm 0.1 N methanol/HCl solution of the 9-diazonium salt (1 g). The mixture was then stirred at room temperature for 4 hours and the product was obtained by precipitation into diethyl ether. The solid was collected to yield 87% of the desired product (9-azido doxycycline).

9-$NH_2$-8-Bromo Doxycycline 0.5 g of 9-azido doxycycline was added to 10 mL of HBr in acetic acid (30 wt %) and the reaction was stirred at room temperature for 1 hour. The product was obtained as a yellow powder in 56% yield by preparative C18 HPLC.

8-Bromo Doxycycline 100 mg of 9-amino-8-bromo doxycycline was reacted with 1.1 g of butyl nitrate in 0.1N HCl to produce the 9-diazonium salt of the 8-bromo doxycycline. The reaction was treated with phosphoric acid to yield the product as crude solid. Preparative HPLC produced the product as a yellow solid in 64% yield.

7-Phenyl Tetracycline 7-iodotetracycline (0.37 mmol), 30 mg Pd(PPh$_3$)$_2$Cl$_2$, 10 mg AsPh$_3$, and 6 mg of CuI was dissolved in 25 ml of toluene with stirring. Phenyl tri-n-butyltin (0.050 mL) was added and the solution was refluxed for 6 hours under nitrogen. The solution was then cooled to room temperature, filtered, the solvent removed and the crude residue purified by preparative thin layer chromatography.

Example 2

In Vitro Minimum Inhibitory Concentration (MIC) Assay

The following assay is used to determine the efficacy of tetracycline compounds against common bacteria. 2 mg of each compound is dissolved in 100 μl of DMSO. The solution is then added to cation-adjusted Mueller Hinton broth (CAMHB), which results in a final compound concentration of 200 μg per ml. The tetracycline compound solutions are diluted to 50 μL volumes, with a test compound concentration of 0.098 μg/ml. Optical density (OD) determinations are made from fresh log-phase broth cultures of the test strains. Dilutions are made to achieve a final cell density of $1\times10^6$ CFU/ml. At OD=1, cell densities for different genera should be approximately:

E. coli $1\times10^9$ CFU/ml

S. aureus $5\times10^8$ CFU/ml

Enterococcus sp. $2.5\times10^9$ CFU/ml

50 μl of the cell suspensions are added to each well of microtiter plates. The final cell density should be approximately $5\times10^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

The invention claimed is:

1. A compound of formula (I):

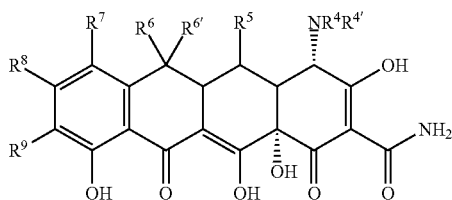

or a pharmaceutically acceptable salt thereof, wherein:
$R^4$ and $R^{4'}$ are each methyl;
$R^5$ is hydrogen or hydroxyl;
$R^6$ and $R^{6'}$ are each independently hydrogen, methyl, or hydroxyl;
$R^7$ is hydrogen, lower alkenyl, lower alkynyl or acyl;
$R^8$ is hydrogen, phenyl, nitrophenyl, or lower alkynyl; and
$R^9$ is hydrogen; provided that at least one of $R^7$ or $R^8$, is not hydrogen, or 8-bromo doxycycline or a pharmaceutically acceptable salt thereof.

2. The compound of claim 1, wherein $R^5$ is hydroxyl, $R^6$ is methyl, and $R^{6'}$ is hydrogen.

3. The compound of claim 2, wherein $R^7$ is ethenyl, ethynyl or acyl, and $R^8$ is hydrogen.

4. The compound of claim 3, wherein said compound is 7-ethenyl doxycycline or 7-ethynyl doxycycline or a pharmaceutically acceptable salt thereof.

5. The compound of claim 3, wherein said compound is 7-acyl doxycycline or 7-acetyl doxycycline or a pharmaceutically acceptable salt thereof.

6. The compound of claim 2, wherein $R^8$ is phenyl, or nitrophenyl; and $R^7$ is hydrogen.

7. The compound of claim 6, wherein said compound is 8-phenyl doxycycline or 8-(p-nitrophenyl) doxycycline or a pharmaceutically acceptable salt thereof.

8. The compound of claim 2, wherein $R^8$ is phenyl or ethynyl.

9. A pharmaceutical composition comprising a therapeutically effective amount of a compound of claim 1 and a pharmaceutically acceptable carrier.

10. A pharmaceutical composition comprising a therapeutically effective amount of a compound and a pharmaceutically acceptable carrier, wherein said compound is selected from the group consisting of: 7-ethynyl doxycycline, 7-acyl doxycycline, 7-ethenyl doxycycline, 8-phenyl-9-amino doxycycline, 8-bromo doxycycline, 8-phenyl doxycycline, 8-(p-nitrophenyl) doxycycline, 7-acetyl doxycycline, 8-ethynyl-9-amino doxycycline and pharmaceutically acceptable salts thereof.

11. A method for treating a bacterial infection in a mammal, comprising administering to said mammal a compound of claim 1.

12. A method for treating a bacterial infection in a mammal, comprising administering to said mammal a compound, wherein said compound is selected from the group consisting of: 7-ethynyl doxycycline, 7-acyl doxycycline, 7-ethenyl doxycycline, 8-phenyl-9-amino doxycycline, 8-bromo doxycycline, 8-phenyl doxycycline, 8-(p-nitrophenyl) doxycycline, 7-acetyl doxycycline, 8-ethynyl-9-amino doxycycline and pharmaceutically acceptable salts thereof.

13. The method of claim 11, wherein said bacterial infection is associated with *E. coli, S. aureus* or *E. faecalis*.

14. The method of claim 12, wherein said bacterial infection is associated with *E. coli, S. aureus* or *E. faecalis*.

* * * * *